US005898114A

United States Patent [19]

Basch et al.

[11] Patent Number: 5,898,114

[45] Date of Patent: Apr. 27, 1999

[54] AIR SAMPLER FILTER CASSETTE CARRIER

[75] Inventors: Lauren R. Basch, East Greenbush; Michael J. Gallo, Voorheesville, both of N.Y.

[73] Assignee: Rupprecht & Patashnick Co., Inc., Albany, N.Y.

[21] Appl. No.: 09/021,592

[22] Filed: Feb. 10, 1998

Related U.S. Application Data

[62] Division of application No. 08/701,763, Aug. 22, 1996, Pat. No. 5,717,147.

[51] Int. Cl.[6] .......... G01N 1/16

[52] U.S. Cl. .......... 73/863.23

[58] Field of Search .......... 73/28.01, 28.04, 73/31.01, 31.02, 31.07, 863.01, 863.21, 863.25, 864.34; 55/270; 209/237, 239

[56] References Cited

U.S. PATENT DOCUMENTS

| | | | |
|---|---|---|---|
| 3,693,410 | 9/1972 | Robrecht . | |
| 3,765,247 | 10/1973 | Riggs | 73/421.5 |
| 4,080,832 | 3/1978 | Moody et al. . | |
| 4,786,472 | 11/1988 | McConnell et al. . | |
| 5,235,190 | 8/1993 | Tucker et al. . | |
| 5,468,968 | 11/1995 | Bailey et al. . | |
| 5,551,311 | 9/1996 | Ogden et al. | 73/28.01 |
| 5,571,946 | 11/1996 | Koshi et al. | 73/28.01 |
| 5,604,335 | 2/1997 | Isahaya | 73/28.01 |

FOREIGN PATENT DOCUMENTS

| | | |
|---|---|---|
| 1163380 | 3/1984 | Canada . |
| 0 034 863 | 9/1981 | European Pat. Off. . |
| 30 30 188 | 12/1982 | Germany . |
| WO 93/06910 | 4/1993 | WIPO . |
| WO 94/29716 | 12/1994 | WIPO . |

OTHER PUBLICATIONS

Chow et al., “A Sampling System for Reactive Species in the Western U.S.”, Aug. 1990, pp. 1–31.

Rogers, et al., “Design and Testing of a New Size Classifying Isokinetic Sequential Aerosol Sampler”, JAPCA Journal, vol. 39, No. 12, Dec. 1989, pp. 1569–1576.

*Primary Examiner*—Robert Raevis
*Attorney, Agent, or Firm*—Heslin & Rothenberg, P.C.

[57] ABSTRACT

A carrier supporting multiple filters is inserted jointly with the filters into an air sampler. The carrier includes an indexing structure to ensure correct positioning within the air sampler. A memory device physically associated with the carrier stores sample collection data provided by the air sampler. The stored data can be read by a read/write station at a lab, and transmitted to a processor. The processor also receives a weight reading from a communicating balance for each collected sample, and calculates therefrom mass concentration for each sample.

4 Claims, 8 Drawing Sheets

30 78 84 82 66 80 76

12
14
20
10
16
18
56
54
58
22
67
32
30
24
28
52
38
26
34
50
36
36
60
40
64
62
46
48
44
42
F1
F2
F3
F4
F5
1
2
3
4
5
6
7
8
9
0
+

24
18
68
22
72
32
66
30
70
74
28
38

30
84
82
78
66
80
76

12
14
20
16
10'
18'
32'
56
54
58
67
30'
28'
24'
52
F1
F2
F3
F4
F5
26
36'
50
60
64
62
40'
48
44
42

AIR SAMPLER
(INCLUDES READ / WRITE DEVICE FOR CARRIER MEMORY)
10
30
84
CARRIER PROBE
106
CASSETTE PROBE
104
MEMORY READ / WRITE STATION
102
100
PC
108
BALANCE FOR WEIGHING FILTERS
110
PRINTER
112
FIELD
LABORATORY

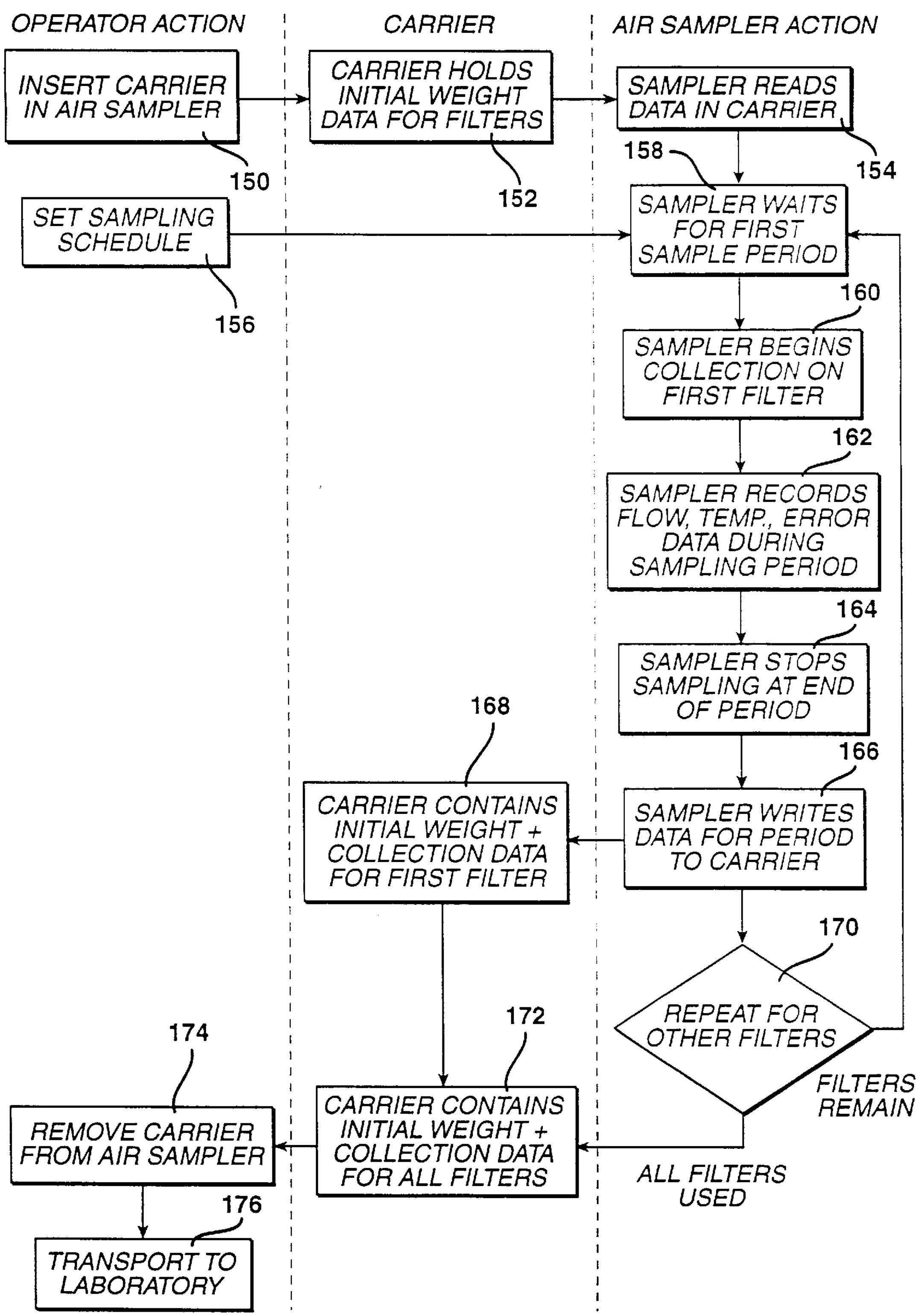
FIG. 9
OPERATOR ACTION
CARRIER
AIR SAMPLER ACTION
INSERT CARRIER IN AIR SAMPLER
150
CARRIER HOLDS INITIAL WEIGHT DATA FOR FILTERS
152
SAMPLER READS DATA IN CARRIER
154
SET SAMPLING SCHEDULE
156
158
SAMPLER WAITS FOR FIRST SAMPLE PERIOD
160
SAMPLER BEGINS COLLECTION ON FIRST FILTER
162
SAMPLER RECORDS FLOW, TEMP., ERROR DATA DURING SAMPLING PERIOD
164
SAMPLER STOPS SAMPLING AT END OF PERIOD
166
SAMPLER WRITES DATA FOR PERIOD TO CARRIER
168
CARRIER CONTAINS INITIAL WEIGHT + COLLECTION DATA FOR FIRST FILTER
170
REPEAT FOR OTHER FILTERS
FILTERS REMAIN
ALL FILTERS USED
172
CARRIER CONTAINS INITIAL WEIGHT + COLLECTION DATA FOR ALL FILTERS
174
REMOVE CARRIER FROM AIR SAMPLER
176
TRANSPORT TO LABORATORY

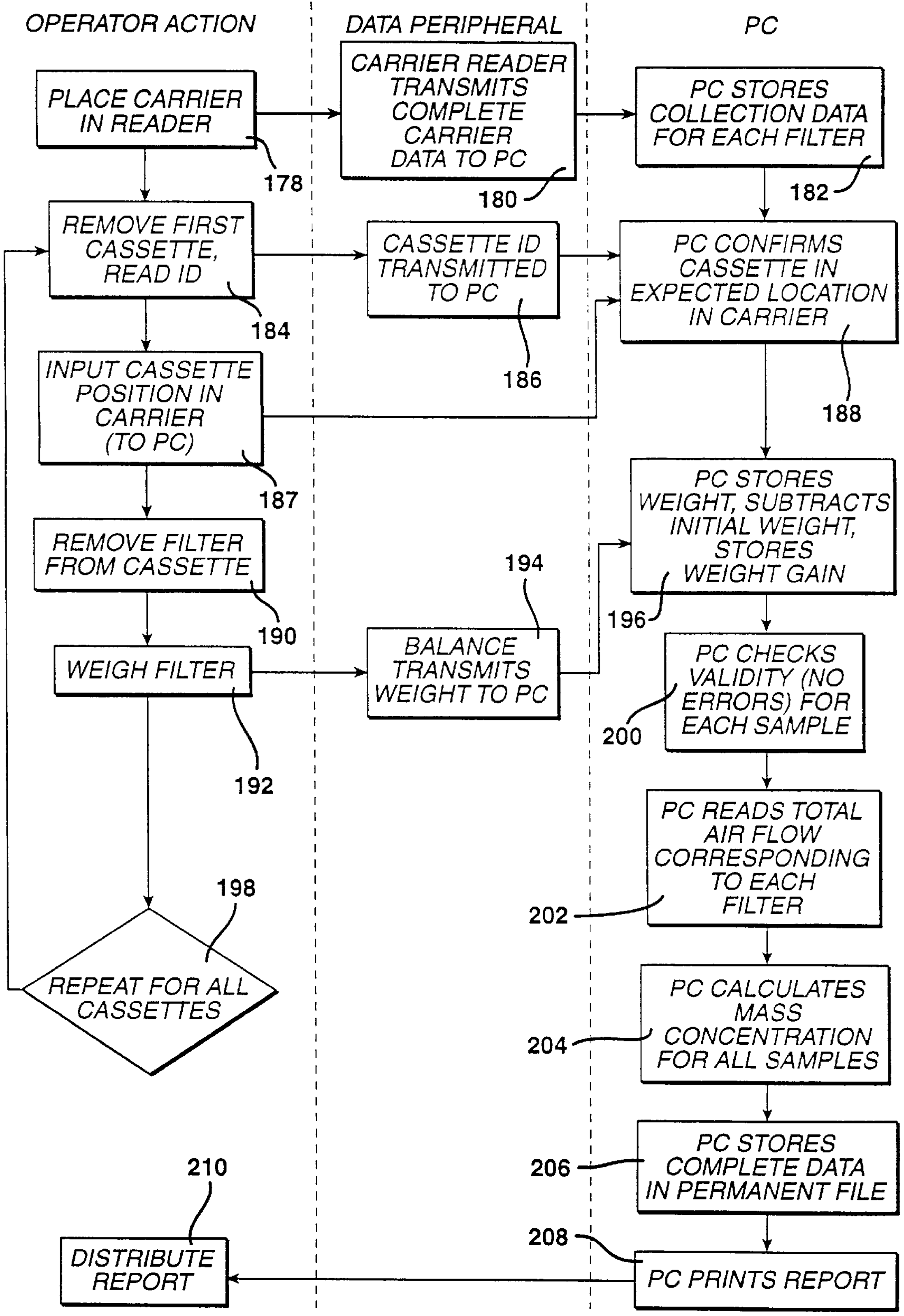
FIG. 10
OPERATOR ACTION
DATA PERIPHERAL
PC
PLACE CARRIER IN READER
178
CARRIER READER TRANSMITS COMPLETE CARRIER DATA TO PC
180
PC STORES COLLECTION DATA FOR EACH FILTER
182
REMOVE FIRST CASSETTE, READ ID
184
CASSETTE ID TRANSMITTED TO PC
186
PC CONFIRMS CASSETTE IN EXPECTED LOCATION IN CARRIER
188
INPUT CASSETTE POSITION IN CARRIER (TO PC)
187
REMOVE FILTER FROM CASSETTE
190
194
PC STORES WEIGHT, SUBTRACTS INITIAL WEIGHT, STORES WEIGHT GAIN
196
WEIGH FILTER
BALANCE TRANSMITS WEIGHT TO PC
PC CHECKS VALIDITY (NO ERRORS) FOR EACH SAMPLE
200
192
PC READS TOTAL AIR FLOW CORRESPONDING TO EACH FILTER
202
198
REPEAT FOR ALL CASSETTES
PC CALCULATES MASS CONCENTRATION FOR ALL SAMPLES
204
PC STORES COMPLETE DATA IN PERMANENT FILE
206
210
DISTRIBUTE REPORT
208
PC PRINTS REPORT

AIR SAMPLER FILTER CASSETTE CARRIER

This application is a division of Ser. No. 08/701,763, filed Aug. 22, 1996, now U.S. Pat. No. 5,717,147.

TECHNICAL FIELD

The present invention relates, in general, to air samplers for collecting and analyzing airborne particulates, and more particularly, to an improved filter carrier for use in such equipment.

BACKGROUND ART

Nowadays, the amount of particulate matter in atmospheric air is commonly measured with a device called an air sampler. The air sampler draws a measured volume of air through a filter over a predetermined period of time, typically 24 hours. The weight gain of the filter, measured before and after sampling under identical conditions of temperature and humidity, divided by the volume of air passed through the filter equals the mass concentration of particulate expressed in mass per actual cubic meter of air or mass per standard cubic of air. Generally, a size selective inlet is used on an air sampler to remove particles which are greater than a certain size, for instance 10 microns or 2.5 microns, from the air, prior to particulate collection by the filter.

Most current air samplers use a single filter which must be changed after every sampling period. Newer samplers use multiple filters, each in an individual cassette, which are selected sequentially. This allows the sampler to be active for multiple individual sampling periods without operator attention. However, the multiple filter exchange procedure is time consuming, labor intensive, and may lead to errors. Typically, each filter cassette is held by an individual cassette holder which is connected to a multi-station manifold or plenum through which passes the sample stream. Each of these filter holders must be opened individually in the field, and the cassette exchanged. This has the disadvantage of requiring handling of multiple cassettes under adverse conditions which can lead to filter contamination or misidentification.

Ideally, each filter cassette should be unambiguously identified and coordinated with the appropriate sample collection data such as time and date, total sample volume, flow rates, temperature, barometric pressure, humidity and any sampler error codes. Normally, such data is read from the air sampler and manually recorded in a notebook. In the field, the data is often collected under adverse weather conditions which makes its recording subject to human error. It would be desirable to eliminate this manual data transfer in the field, as well as the manual data taking and calculation involved in weighing the filters and reporting the final resulting mass concentrations measured by the air sampler.

In a paper entitled "A Sampling System For Reactive Species In The Western U.S.", (August 1990), Chow et al. describe a sampling system for collection of gases and particles on multiple stacked filter media, using filter holders which are apparently individually mounted in situ, to a sampler plenum. This system collects suspended particulate matter in $PM_{2.5}$ (2.5 ppm) and $PM_{10}$ (10 ppm) size fractions on media suitable for measurement of mass, chloride nitrate, sulfate, sodium, magnesium, potassium, and calcium ion concentrations. Gas-absorbing filters are used for the measurement of sulphur dioxide, nitrogen dioxide, nitric acid and ammonia. The versatility and utility of air samplers in measuring and monitoring atmospheric concentrations of pollutants is clearly described in this paper (the full contents of which is incorporated by reference herein).

A centrally controlled multi-station airborne particulate sampling system is described in commonly assigned International Patent Publication No. WO 94/29716 (the full contents of which is herein incorporated by reference). In this system, a paired intake and particulate filter is located in a hub unit and in each of multiple satellite units coupled to the hub unit. A vacuum pump and sampling process controller in the hub unit facilitate sequential sampling through the intake-filter pairs at the different units. This sampling system also includes a unique filter holder exchange mechanism, volume flow control, external condition activation, and sampling temperature control.

Although such known multiple filter air samplers provide significant benefits, they continue to suffer from the drawbacks described above. A need thus persists for an air sampler which can overcome these drawbacks.

SUMMARY OF THE INVENTION

This need is satisfied, and other major advantages realized, in accordance with the principles of the present invention, by the provision of a filter carrier which facilitates joint insertion of multiple filters and the carrier into an air sampler and/or which is capable of receiving and storing data associated with a filter supported by the carrier. An air sampler, and mass concentration determining method and apparatus, compatible with said carrier, are also provided.

Briefly summarized, the present invention comprises, in one aspect, a multiple filter carrier for use in a manual air sampler. A portable base plate of the carrier has multiple throughholes and supports multiple filters juxtaposed these holes. The carrier is configured for insertion jointly with the filters into the air sampler. The carrier advantageously includes indexing means for ensuring its correct positioning within the air sampler. Optionally, the carrier also includes memory means for storing data related to the filters. Such data can include a unique filter identification for each supported filter, as well as filter correlated sample collection data provided by the air sampler.

The filters of the present invention are preferably mounted in individual filter holders or cassettes for easy and safe handling. The cassettes are supported by the multiple filter carrier of the present invention, and in one embodiment a first portion of each cassette is joined to the base plate of the carrier while a second removable cassette portion provides access to mount a corresponding filter in the cassette. Each cassette preferably also includes a unique machine-readable cassette identifier. The identifier distinguishes the filter carrier by the associated cassette from other filters of the same type.

In another aspect, the present invention provides an improved portable filter holder for an air sampler which incorporates memory means for receiving and storing sample collection data provided by said air sampler. The memory means is preferably a memory chip which stores data relating to at least one filter carried by the holder.

The present invention also contemplates a method of collecting samples of airborne particulate over several sampling periods. In this method, multiple filters are supported juxtaposed respective laterally spaced openings in a common filter carrier. The carrier with the filters is inserted into an air sampler and then samples of airborne particulate are sequentially collected on the filters for respective sampling periods. The carrier, along with the support filters and collected samples, are jointly removed from the air sampler for transport to a measurement site. Preferably, filter correlated sample collection data provided by the air sampler is recorded in memory means associated with the carrier. After transport to the measurement site, the filter correlated sample collection data is retrieved from the memory means of the carrier. The weight of each collected sample is determined, and mass concentration for each sample is calculated from this data and weight.

Preferably, the measurement and analysis process is highly automated, employing a balance which transmits a resulting weight reading to a processor. The retrieved filter correlated sample collection data from the memory means of the carrier is also transmitted to the processor. The processor calculates and outputs the mass concentration for each sample.

In yet another aspect, the present invention provides an air sampler for collecting samples of airborne particulate on multiple filters. The sampler includes an air inlet and a carrier supporting multiple laterally spaced filters. The filters are jointly inserted and removed from the sampler with the carrier. The sampler further includes means for producing air flow into the inlet and through the filters in order to collect airborne particulate on respective filters. Air control means selectively channel air flow through respective filters for respective sampling periods. The air control means can include an upper air distribution plate and a lower air distribution plate sandwiching therebetween the carrier. Each air distribution plate has throughholes aligned with each carrier supported filter. The upper distribution plate and lower distribution plate are brought into sealing engagement with the carrier prior to air sampling. Air hose fittings are mounted to the lower distribution plate while an air plenum is located between the inlet and the upper distribution plate.

In a particularly advantageous aspect of the present invention, the plenum, upper air distribution plate, carrier and supported multiple filters, lower distribution plate and air hose fittings are readily replaceable with a single filter carrier and associated air directing assembly, for reference sampling. This simple mechanical substitution allows a single air sampler to be used for multiple applications.

In a further aspect, the present invention provides an air sampler for collecting samples of airborne particulate. The sampler includes an air inlet, a filter holder supporting at least one filter, means for producing air flow into said inlet and through said filter, a memory device physically associated with the filter holder, and means for automatically recording sample collection data in the memory device.

According to a still further aspect of the present invention, apparatus for determining mass concentration of a collected particulate sample on a carrier supported filter is provided. The apparatus includes means for retrieving sample collection data from a memory device physically associated with the carrier and transmitting the received data, in combination with a processor for receiving the data and calculating mass concentration therefrom. A balance weighs the collected particulate sample and transmits a resulting weight reading to the processor for use in calculating the mass concentration. An output device can be connected to the processor for automatically outputting a report of the mass concentration. This apparatus, in conjunction with the filter carrier having a memory device, and an air sampler having means for automatically recording sample collection data in the memory device, provides a system for automating analysis of collected particulate samples.

The air sampling apparatus and methods of the present invention, as manifested in the above-described multiple aspects, provide many significant advantages. The multiple filter carrier allows all filters of the air sampler to be exchanged simultaneously. Thus, the interruption in sampling is minimized. No handling of the individual filter cassettes is required, minimizing the chance of contamination. The filter cassettes are ordered in the carrier, and this order is not disturbed. This minimizes the chance of losing the identity of an individual cassette. Further, in the carrier, the filter cassettes may be closely spaced allowing for a smaller, more compact air sampler. The carrier also acts as an aid in organizing and maintaining identity in subsequent laboratory conditioning and weighing of the filters.

The carriers of the present invention make filter exchange faster, easier and more convenient. They reduce handling in the field where weather conditions can be extreme and avoid mix up of the cassettes in the field and elsewhere. The chance for errors and the labor required both in the field and the laboratory are minimized. Sample collection data and the associated filter are kept together and unambiguously correlated. The carrier memory, writable at the air sampler and readable at the laboratory, when integrated with a communicating balance and a processor allows calculation and outputting of mass concentration measurements in a highly automated fashion, with minimal operator intervention.

BRIEF DESCRIPTION OF THE DRAWINGS

These and other objects, advantages and features of the present invention will be more readily understood from the following detailed description of certain preferred embodiments of the present invention, when considered in conjunction with the accompanying drawings in which:

FIG. 9 is a flow diagram depicting a sampling process of the present invention; and FIG. 10 is a flow diagram illustrating a post sampling process of the present invention.

DETAILED DESCRIPTION

Figure 1:
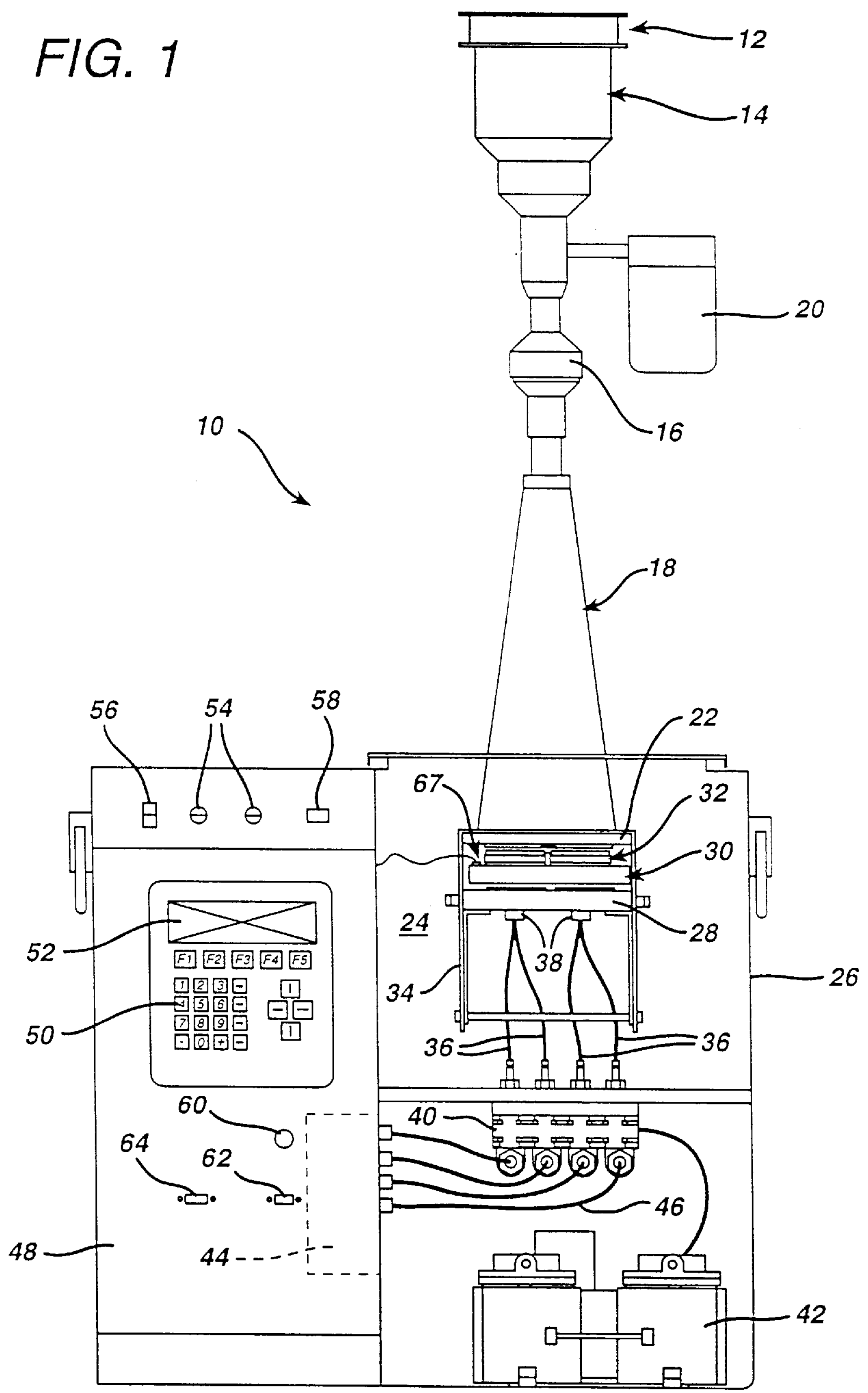
FIG. 1 is an elevational view of an air sampler constructed in accordance with the principles of the present invention.

Referring now to the drawings, in which the same reference numbers are used throughout multiple figures to designate the same or similar components, FIG. 1 illustrates an air sampler, constructed in accordance with the principles of the present invention for use in a "manual sampling" technique for the measurement of ambient particulate concentrations. "Manual sampling" employs a filter in a field unit to continuously sample airborne solid particulates passing therethrough over a defined period of time. The filter is then manually removed from the field unit and returned to a laboratory for exact measurement of particulate mass collected by the filter.

In the air sampler 10 depicted in FIG. 1, an airstream enters air entry or intake 12 and passes through a $PM_{10}$ inlet 14 and a $PM_{2.5}$ impactor 16 into plenum 18. A water collector 20 can be employed to remove condensed water from the air stream. Entry 12, inlet 14, impactor 16 and water collector 20 are well known and commercially available. Plenum 18, preferably in the shape of a truncated pyramid, has, in known fashion, side walls angled to minimize particle losses along the walls. Cone or other shaped plenums may also be used.

Plenum 18 is preferably secured to an upper distribution plate 22 of an air distribution subassembly 24 within housing 26. Subassembly 24, which is shown in its closed sealing operative position in FIG. 1, also includes a lower distribution plate 28. Upper distribution plate 22 and lower distribution plate 28 sandwich a multiple filter carrier 30 supporting multiple filter cassettes 32. Further details of the cassette 32, carrier 30, and air distribution subassembly 24 are provided hereinafter with reference to FIGS. 4 and 5, FIG. 3, and FIG. 2, respectively.

Referring still to FIG. 1, air distribution subassembly 24 further includes a filter carrier exchange mechanism 34 which facilitates separation of lower distribution plate 28 and carrier 30 from upper distribution plate 22 and subsequent joint removal and substitution of carrier 30 and associated filter cassettes 32. Exchange mechanism 34 may comprise any suitable mechanical linkage which permits the lower distribution plate 28 to be separated from upper plate 22 and easy access for exchange of multiple filter carrier 30 with its associated filter cassettes 32. The filter holder exchange mechanism of published International Application WO 94/29716 can be adapted and used for this purpose.

Air hoses or tubing 36 extend from fittings 38, on the bottom of lower distribution plate 28, to solenoid valves 40. Valves 40 are pneumatically connected to vacuum pump 42 and are controlled by a processor 44 through electrical cables 46. Vacuum pump 42 produces an air stream which is channeled through a particular filter cassette 32 by activation of an appropriate processor controlled solenoid valve 40.

Processor or process controller 44 is located behind a panel 48. Panel 48 supports a keypad 50 and display 52, as well as other conventional features including fuses 54, power switch 56, status light 58, display contrast adjustment knob 60, and RS-232 port 62, and an auxiliary input/output port 64. Preferably, the air sampler also includes a connector or probe 67 for facilitating data communication between processor 44 and a memory device on carrier 30, as more fully described hereinafter. Other electronics, sensors, transducers and equipment (not shown) may be disposed behind panel 48 for use, for example, as described in International Publication WO 94/29716.

Figure 2:
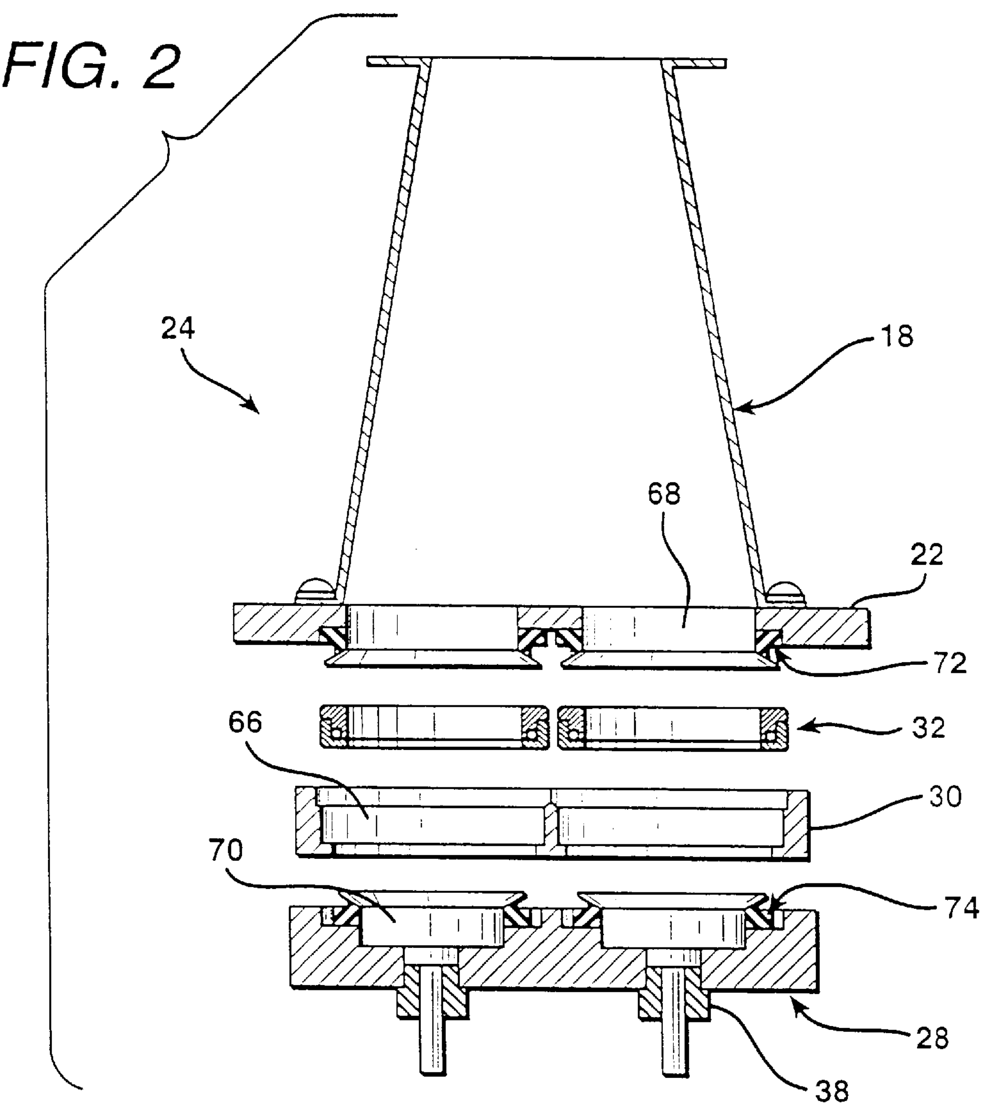
FIG. 2 is an exploded cross-sectional view of an air distribution subassembly of the sampler of FIG. 1.

FIG. 2, for purposes of clarity, depicts the air distribution subassembly 24 in exploded view. As discussed in greater detail hereinafter with reference to FIG. 3, carrier 30 has multiple throughholes 66. A like number of filter cassettes 32 are supported by the carrier juxtaposed throughholes 66. Each of the air distribution plates 22 and 28 have a matching number of throughholes 68 and 70 aligned with respective filter cassettes 32. Seals 72 and 74 on the upper and lower distribution plates respectively ensure an air-tight connection when the lower distribution plate 28, carrier 30 and upper distribution plate 22 are brought into pressing engagement.

Figure 3:
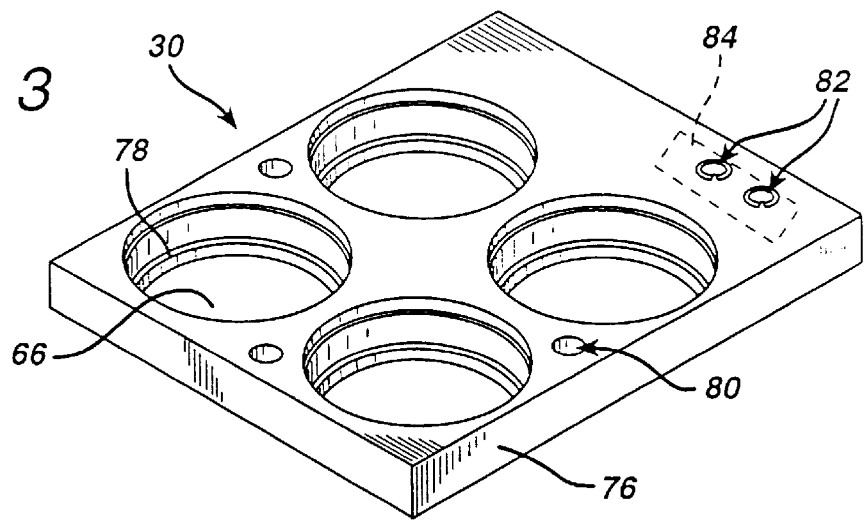
FIG. 3 is an isometric view of a multiple filter carrier of the present invention.

Referring now to FIG. 3, multiple filter carrier 30 comprises a base plate 76 having multiple laterally spaced throughholes 66. Each throughhole 66 can include a ledge 78 for receiving and engaging an individual filter cassette 32. Base plate 76 is preferably substantially planar and may be made of a metal, e.g. aluminum, plastic or other suitable mechanically and chemically stable, lightweight, and air impervious material. Although four throughholes 66 are shown in FIG. 3, the number, size and shape of such holes may vary.

Carrier 30 is preferably provided with indexing or keying means to ensure one-way insertion and correct positioning of the carrier within the air sampler. Three locating pins 80 can be used to achieve this indexing function. Alternatively, the shape of the base plate itself, or other indexing approaches may be employed to establish the desired unambiguous relationship between filters in the carrier and the air sampler.

Also shown in FIG. 3 are contacts 82 for a figuratively depicted integrated circuit memory chip 84 physically incorporated with carrier 76. Memory chip 84 serves to store data relating to filters supported by carrier 76. This data may include identification information for each of the filters or filter cassettes and/or filter correlated sample collection data provided by the processor 44 of air sampler 10 through probe 67. During each filter's collection period, the processor of the air sampler updates the memory device or chip 84 with the active filter position within the carrier, sample flow, meteorological data, error flags, or any other pertinent data. Such sample collection data is thus unambiguously associated with the particulate sampling filter. The information is recorded in memory chip 84 for transport with the filters back to the laboratory or other measurement site. When the entire carrier and its associated filters are returned to the laboratory, the memory chip can be read by an appropriate probe and reading device to retrieve the data for mass concentration or other analysis purposes. Memory device 84 preferably consists of a non-volatile electronic memory chip, such as the 64 Kbit Touch Memory™ device DS1996 commercially available from the Dallas Semiconductor Corporation. Other comparable integrated circuit memory chips, or other equivalent memory devices could also be employed. Chips with additional intelligence or functionality might also be employed with the carrier.

Figure 4:
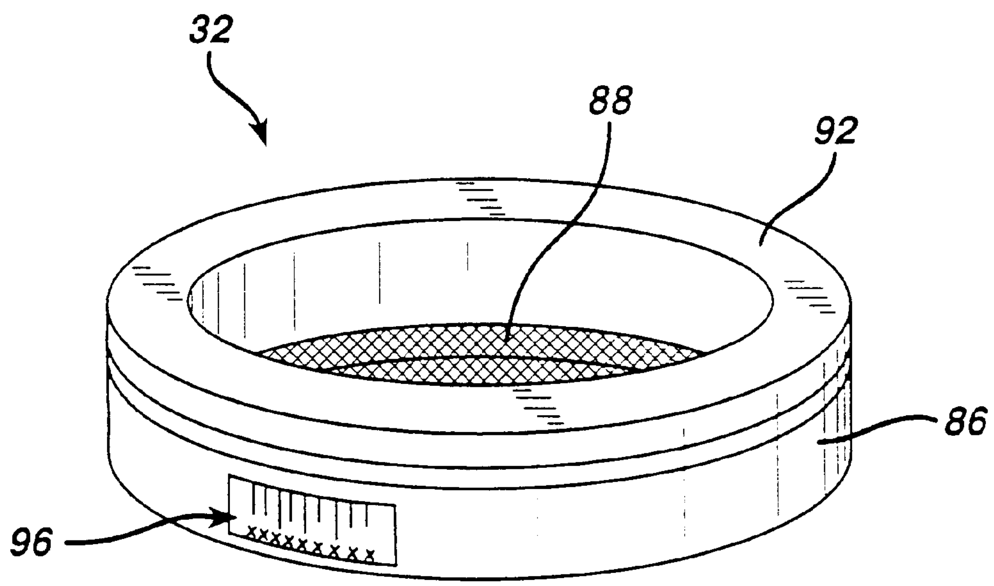
FIG. 4 is an isometric view of a filter holder cassette.
Figure 5:
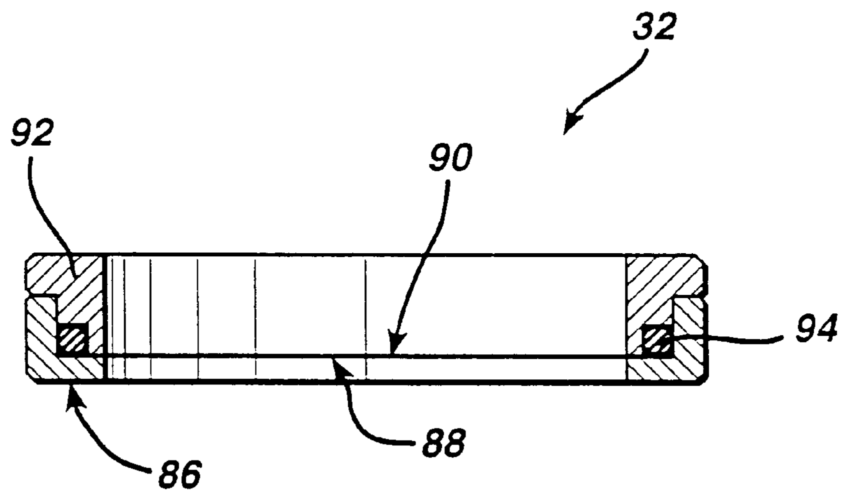
FIG. 5 is a cross-sectional elevational view of the cassette of FIG. 4.

A suitable filter cassette 32 for use with carrier 30 is depicted in FIGS. 4 and 5. Cassette 32 comprises an individual filter holder which can be easily inserted and supported in throughholes 78 of carrier 30. Cassette 32 has a lower annular ring 86 which supports a central screen 88. A filter disk 90, substantially coextensive with screen 88 is sealed around its rim and secured in place on top of screen 88 by a press fit (or otherwise secured) retaining ring 92. An "O" ring 94 ensures an airtight peripheral seal within the cassette. A bar code label 96 or other machine-readable identifier is secured to cassette 32 and advantageously used to uniquely identify a filter mounted in cassette 32. For positive identification purposes, an individually serialized, read-only, integrated circuit chip (not shown), such as chip DS2401 from Dallas Semiconductor Corporation, can be embedded in or otherwise physically associated with the cassette.

Figure 6:
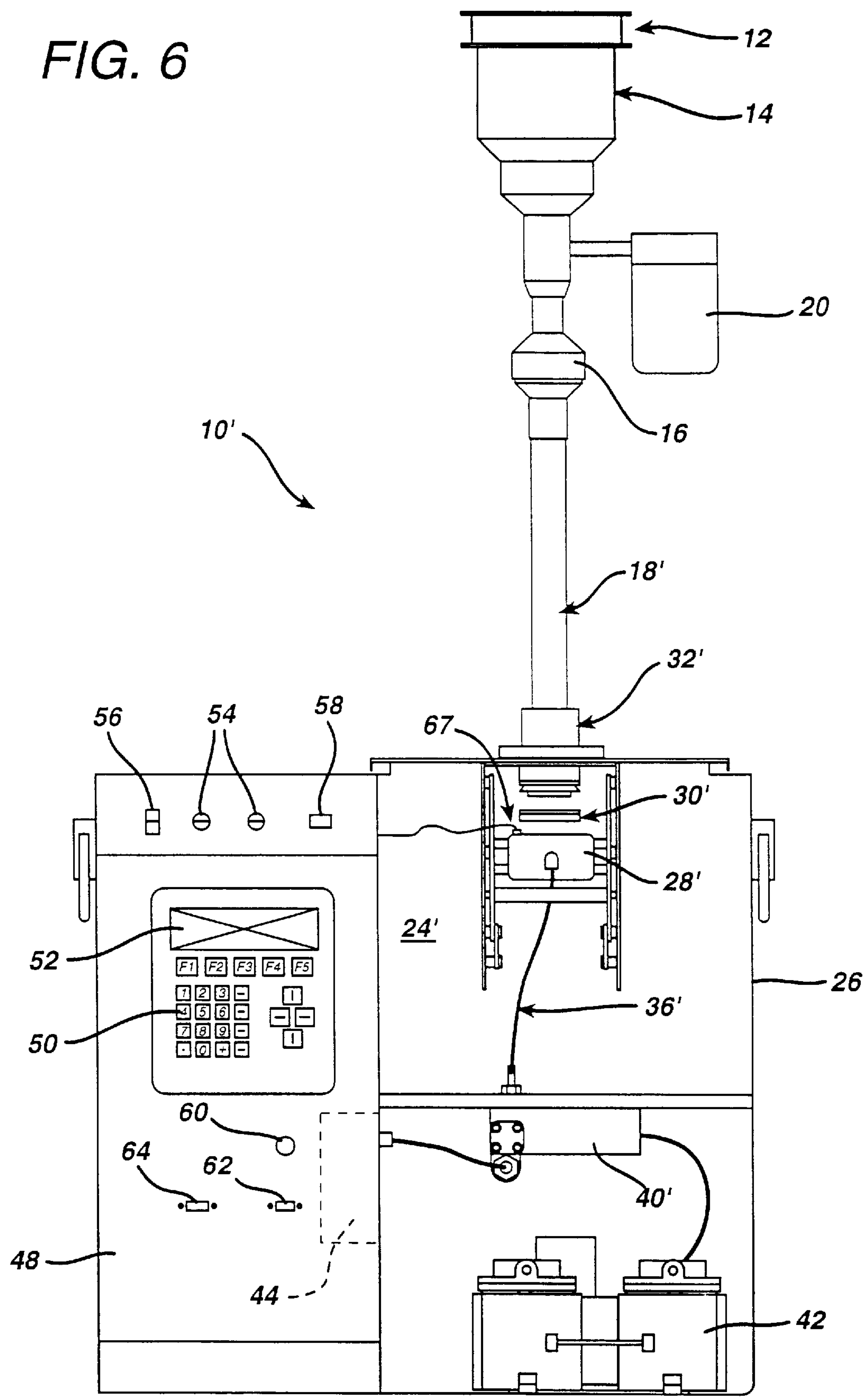
FIG. 6 is an elevational view illustrative of the ready convertability of the air sampler of the present invention.

FIG. 6 illustrates an important advantage of the present invention, i.e. its ready convertability from a multiple filter air sampler to a single filter reference sampler. In this drawing, identical components have the same reference number, while reference numbers for similar or substitute elements have a prime. Conversion of the multiple filter air sampler 10 of FIG. 1 into a single filter reference sampler 10' merely requires a simple mechanical substitution of a single filter air direction subassembly 24' for air distribution subassembly 24. As shown in FIG. 6, individual filter holder 30' is positioned between an upper cassette holder 32' and lower cassette holder 28'. Instead of a plenum, a simple air conduit 18' can be employed. Optionally, probe 67 can be used to download sample collection data, or otherwise communicate with a memory device (not shown) physically associated with holder 30'. Aside from the single air stream, reference sampler 10' can operate identically to multiple filter sampler 10. The versatility of the present invention in allowing the same instrument to serve as either a multiple filter sampler or a single filter reference sampler provides a significant cost advantage to the user.

Figure 7:
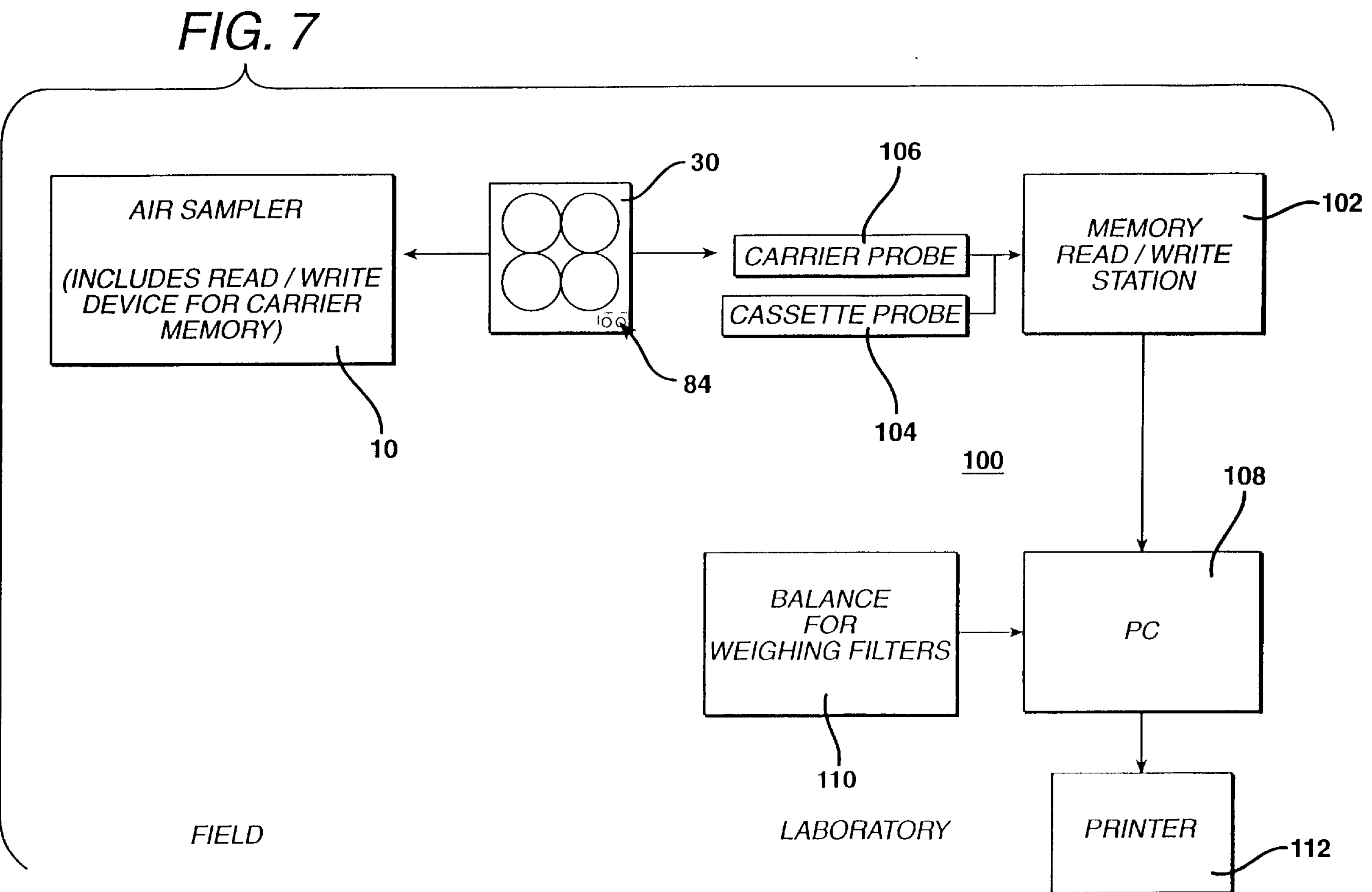
FIG. 7 is a block diagram of a system for automating analysis of collected particulate samples, according to the principles of the present invention.

FIG. 7 illustrates in schematic form how carrier 30 with incorporated memory device 84 can be used to communicate data between air sampler 10 in the field and a laboratory measurement site 100. To take maximum advantage of the data memory capabilities of carrier 30, measurement site 100 is provided with a memory read/write station 102. Through a cassette probe 104 and a carrier probe 106, respectively, station 102 can read cassette identifier 96 and retrieve data from memory device 84 of carrier 30. Station 102 transmits this data to a processor 108. Processor 108 also receives a weight reading from a communicating balance 110. Balance 110 may comprise a gravimetric balance outfitted with an RS-232 communication link. With the sample collection data provided by station 102 and the weight reading from balance 110, processor 108 calculates mass concentration of collected particulate samples and can automatically provide suitable reports through printer 112 or other output devices.

Figure 8:
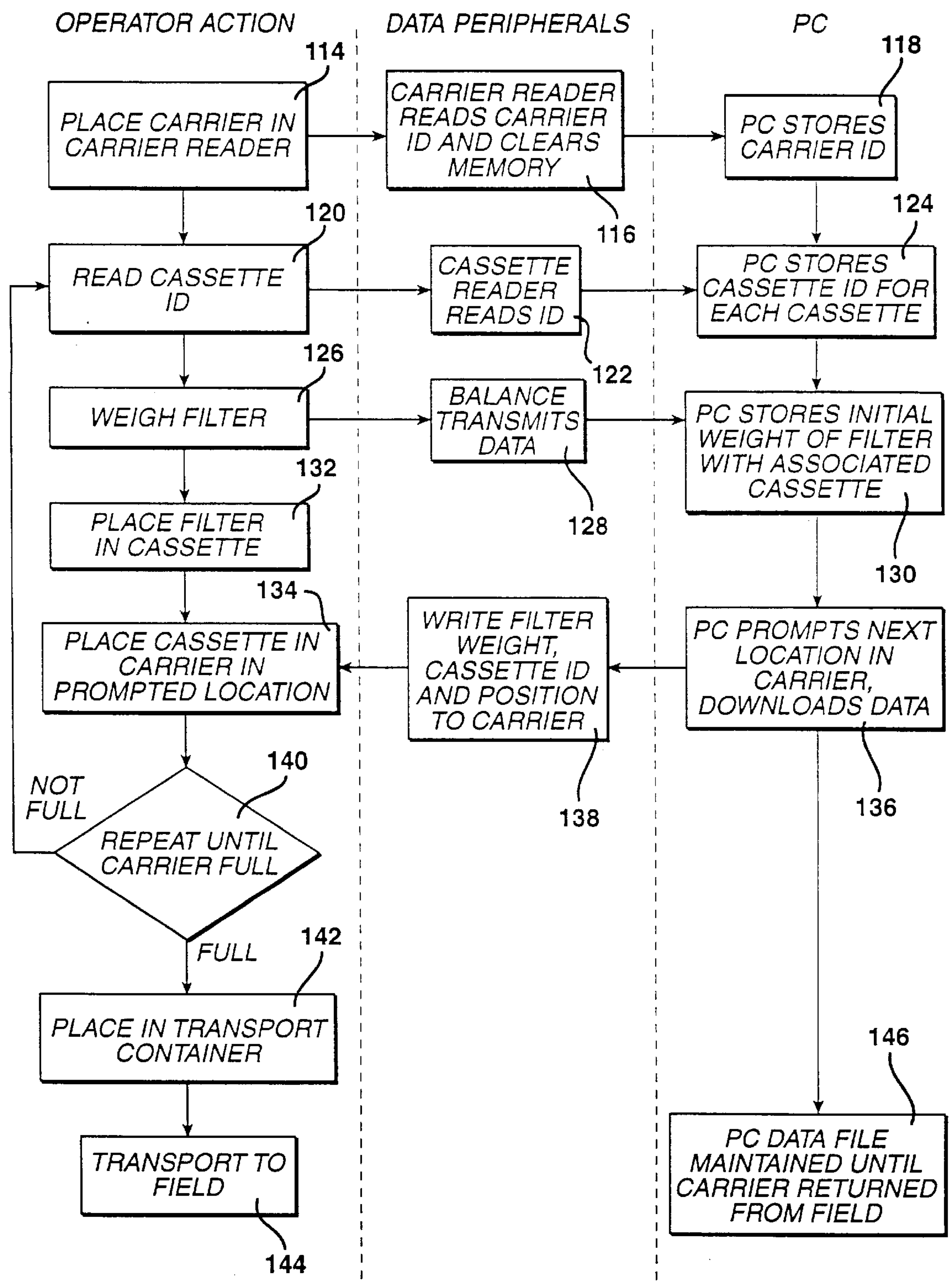
FIG. 8 is a flow diagram illustrating a pre-sampling process of the present invention.

The overall operation of the air sampling and analyzing system of the present invention will now be described with reference to FIGS. 8–10. As illustrated in FIG. 8, prior to sampling, an operator, using carrier probe 106, reads a carrier ID and clears memory 84 of the carrier (steps 114, 116). Memory read/write station 102 transmits the carrier ID to processor (PC) 108 which stores the carrier ID (step 118). The cassette ID for a first cassette is then read with cassette probe 104 (steps 120, 122), and then station 102 transmits the cassette ID to processor 108 for storage (step 124). A filter disk 90 to be inserted in the first cassette is then equilibrated, if necessary, and weighed (step 126). Balance 110 transmits the weight reading to processor 108 (step 128). The processor stores the initial weight of the filter disk with the associated cassette ID (step 130). The operator then places the filter in the first cassette (step 132) and places this cassette in the carrier 30 in a location prompted by the processor (step 134). Processor 108 not only prompts the next location in the carrier but also downloads the filter weight, cassette ID and position to memory 84 of carrier 30 through station 102 and carrier probe 106 (steps 136, 138). These steps are repeated until the carrier is full of filters and then the carrier is placed in a container and transported to air sampler 10 in the field (steps 140, 142, 144). The processor's data file is maintained until the carrier is returned from the field (step 146).

Turning now to FIG. 9, in the field, the operator inserts the carrier with the multiple filters into the air sampler, and the sampler reads the data stored in the memory device of the carrier (steps 150, 152, 154). The operator then sets the desired sampling schedule (step 156). The sampler waits for the first sample period and then begins collection on the first filter (steps 158, 160). The sampler records sample collection data such as air flow, temperature, and error data (e.g. error codes indicating that the sampler was operating outside of its normal performance parameters) during the sampling period and then stops sampling at the end of the scheduled sample period (steps 162, 164). The sampler then writes the sample collection data for the first sample period to the memory of the carrier (step 166). The memory thus contains the initial weight and the sample collection data for the first filter (step 168). The same steps are repeated for all of the remaining filters so that eventually the carrier memory contains an initial weight and sample collection data for all filters of the carrier (steps 170, 172). The operator then removes the carrier along with the filters from the air sampler and transports same back to the laboratory (steps 174, 176).

As shown in FIG. 10, back in the lab, the complete carrier memory data is retrieved with carrier probe 106, and memory read/write station 102 transmits this data to processor 108 (steps 178, 180). The processor stores sample collection data for each filter (step 182). The operator then removes the first cassette and reads the cassette ID with cassette probe 104 (step 184). Station 102 transmits the cassette ID to processor 108. The operator also inputs the cassette position in the carrier to processor 108 (step 187). The processor then confirms that the first cassette is in the expected location in the carrier (step 188). Next, the operator removes the filter from the first cassette, reequilibrates, if necessary, and weighs the filter (steps 190, 192). Communicating balance 110 transmits the resultant weight to processor 108 (step 194). The processor stores the resultant weight, subtracts the initial weight, and stores the weight gain (step 196). This process is repeated for all cassettes (step 198). Processor 108 further checks validity (i.e. no errors in sampling conditions) for each sample, reads the total air flow corresponding to each filter and then calculates mass concentration for all samples (steps 200, 202, 204). The complete data can be stored by the processor in a permanent file and a report printed by the processor for distribution (steps 206, 208 and 210).

The present invention represents a significant advance in the field of air sampling. The multiple filter carrier is easily and quickly exchangeable saving time and minimizing operator exposure to adverse conditions in the field. The built-in memory of the carrier avoids the difficulties associated not only with recording data in the field but also ensuring that the recorded data is correctly associated with the appropriate filter. Also, the carrier memory in conjunction with the memory read/write station and communicating balance at the measurement site permits rapid automated calculation of mass concentration and/or other sample analyses. The savings in labor and enhancement of accuracy in data communication are further complimented by the air sampler's ready convertability from a multiple filter instrument into a single filter reference sampler.

Although specific embodiments of the present invention have been illustrated in the accompanying drawings and described in the foregoing detailed description, it will be understood that the invention is not limited to the particular embodiments described herein, but is capable of numerous rearrangements, modifications and substitutions without departing from the scope of the invention. For example, the present invention can be applied to "high volume samplers" and "dichotomous samplers", and to the measurement of other properties of collected particulate (regardless of the medium in which the particulate is originally suspended) or other types of collected samples. The following claims are intended to encompass all such modifications.

What is claimed is:

1. In a portable filter holder for an air sampler, the improvement comprising memory means for receiving and storing sample collection data provided by said air sampler, said memory means being physically incorporated with said portable filter holder and transported with said holder into and out of said air sampler.

2. The portable filter holder of claim 1, wherein said holder comprises a carrier of multiple filters, and said memory means stores filter correlated sample collect ion data provided by said air sampler.

3. The portable filter holder of claim 1, further including indexing means for ensuring correct positioning of said holder within said air sampler.

4. The portable filter holder of claim 3, wherein said indexing means comprises a plurality of locating pins.

* * * * *